(12) United States Patent
Griffith et al.

(10) Patent No.: US 11,260,226 B2
(45) Date of Patent: Mar. 1, 2022

(54) COCHLEAR IMPLANT ASSEMBLIES AND METHODS OF MANUFACTURING THE SAME

(71) Applicant: Advanced Bionics AG, Staefa (CH)

(72) Inventors: Glen A. Griffith, Newbury Park, CA (US); Jeryle L. Walter, Valencia, CA (US)

(73) Assignee: Advanced Bionics AG, Staefa (CH)

( * ) Notice: Subject to any disclaimer, the term of this patent is extended or adjusted under 35 U.S.C. 154(b) by 138 days.

(21) Appl. No.: 16/542,854

(22) Filed: Aug. 16, 2019

(65) Prior Publication Data

US 2021/0046310 A1   Feb. 18, 2021

(51) Int. Cl.
*A61N 1/36* (2006.01)
*A61N 1/375* (2006.01)
*A61N 1/372* (2006.01)

(52) U.S. Cl.
CPC ......... *A61N 1/36038* (2017.08); *A61N 1/375* (2013.01); *A61N 1/37211* (2013.01)

(58) Field of Classification Search
CPC ............... A61N 1/36038; A61N 1/37211; A61N 1/375; H04R 2225/51; H04R 2225/67
USPC ........................................................ 607/57
See application file for complete search history.

(56) References Cited

U.S. PATENT DOCUMENTS

| 6,542,777 | B1* | 4/2003 | Griffith | A61N 1/37229 607/137 |
| 8,497,804 | B2 | 7/2013 | Haubrich et al. | |
| 2010/0109966 | A1* | 5/2010 | Mateychuk | H01Q 1/38 343/841 |
| 2014/0343626 | A1* | 11/2014 | Thenuwara | A61N 1/37229 607/57 |
| 2014/0364714 | A1 | 12/2014 | Ameri et al. | |
| 2017/0026854 | A1 | 1/2017 | Vilhar | |
| 2021/0213179 | A1* | 7/2021 | O'Connor | A61N 1/37223 |

* cited by examiner

*Primary Examiner* — Carl H Layno
*Assistant Examiner* — Jane C Kalinock
(74) *Attorney, Agent, or Firm* — ALG Intellectual Property, LLC

(57) ABSTRACT

An exemplary cochlear implant assembly includes a cochlear implant configured to apply electrical stimulation to the recipient by way of an electrode array, a cochlear implant antenna communicatively coupled to the cochlear implant, and an encapsulant that covers the cochlear implant and the cochlear implant antenna, the encapsulant impregnated with a dielectric material that is configured to confine an electric field around the cochlear implant antenna. Corresponding methods for manufacturing cochlear implant assemblies are also described.

18 Claims, 8 Drawing Sheets

COCHLEAR IMPLANT ASSEMBLIES AND METHODS OF MANUFACTURING THE SAME

BACKGROUND INFORMATION

Cochlear implant systems are used to provide, restore, and/or improve the sense of hearing to recipients with severe or profound hearing loss. Conventional cochlear implant systems include various components configured to be implanted within a recipient (e.g., a cochlear implant, an antenna, and an electrode lead) and various components configured to be located external to the recipient (e.g., a sound processor, a battery, and a microphone).

When the components of the cochlear implant system are implanted within the recipient, the implanted antenna of the cochlear implant system is positioned in close proximity to surrounding tissue, which has a large dielectric constant (also referred to as relative permittivity) and a large dissipation factor. These attributes of the surrounding tissue may cause the electric field near the antenna to penetrate into the surrounding tissue capacitively pulling the inductance associated with the antenna and adding loss. To confine the electric field around the antenna, a guard wire may be provided (e.g., spirally wrapped) around the antenna of a cochlear implant system. In so doing, the electric field around the antenna is dominated by the presence of the guard wire and the effects of the surrounding tissue are mitigated.

Unfortunately, installing and connecting (e.g., welding) a guard wire to a cochlear implant system includes various manually intensive manufacturing operations. For example, to properly position and space spiral windings of a guard wire, an intermediate molding operation is typically performed in which the antenna is covered with a molded encapsulant (e.g., silicone). The guard wire is then manually wrapped around the molded encapsulant, which is a time consuming and manually intensive process. In addition, guard wires used to confine the electric field around an antenna of a cochlear implant typically have a small diameter, which makes them susceptible to impact damage. These aspects associated with guard wires undesirably increase unit costs and/or reduce the durability of implanted components included in a cochlear implant system.

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

DETAILED DESCRIPTION

Cochlear implant assemblies and methods for manufacturing the same are described herein. As will be described in more detail below, an exemplary cochlear implant assembly described herein includes a cochlear implant configured to apply electrical stimulation to a recipient by way of an electrode array, a cochlear implant antenna communicatively coupled to the cochlear implant, and an encapsulant that covers the cochlear implant and the cochlear implant antenna. The encapsulant is impregnated with a dielectric material that is configured to confine an electric field around the cochlear implant antenna.

Cochlear implant assemblies such as those described herein provide various benefits as compared to conventional cochlear implant assemblies. For example, by utilizing a dielectric material to confine an electric field around the cochlear implant antenna instead of, for example, a spirally wrapped guard wire, it is possible to eliminate various manufacturing operations (e.g., manually winding the guard wire, attaching of the guard wire, etc.) associated with conventional cochlear implant assemblies. As such, cochlear implant assemblies such as those described herein are more cost effective and are easier to manufacture than conventional cochlear implant assemblies. In addition, the dielectric material impregnated in the encapsulant may make the cochlear implant assemblies less susceptible to biofilm formation, infection, and/or device failure than conventional cochlear implant assemblies. As such, cochlear implant systems that use cochlear implant assemblies such as those described herein are more robust and potentially have a longer operational life than cochlear implant systems that use conventional cochlear implant assemblies. Other benefits of the cochlear implant assemblies and methods of manufacture thereof described herein will be made apparent herein.

Figure 1:
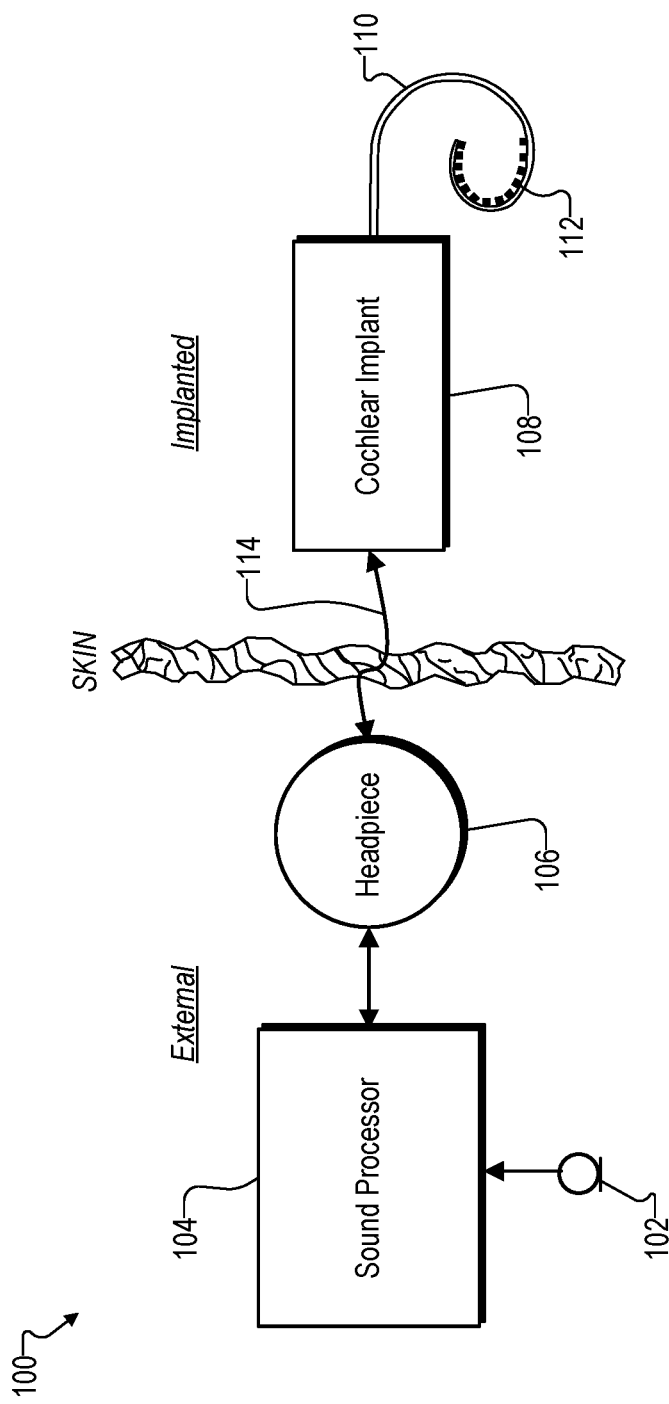
FIG. 1 illustrates an exemplary cochlear implant system according to principles described herein.

FIG. 1 illustrates an exemplary cochlear implant system 100. As shown, cochlear implant system 100 may include various components configured to be located external to a recipient including, but not limited to, a microphone 102, a sound processor 104, and a headpiece 106. Cochlear implant system 100 may further include various components configured to be implanted within the patient including, but not limited to, a cochlear implant 108 and a lead 110 (also referred to as an electrode array) with a plurality of electrodes 112 disposed thereon. As will be described in more detail below, additional or alternative components may be included within cochlear implant system 100 as may serve a particular implementation. The components shown in FIG. 1 will now be described in more detail.

Microphone 102 may be configured to detect audio signals presented to the patient. Microphone 102 may be implemented in any suitable manner. For example, microphone 102 may include a microphone that is configured to be placed within the concha of the ear near the entrance to the ear canal, such as a T-MIC™ microphone from Advanced Bionics. Such a microphone may be held within the concha of the ear near the entrance of the ear canal by a boom or stalk that is attached to an ear hook configured to be selectively attached to sound processor 104. Additionally or alternatively, microphone 102 may be implemented by one or more microphones disposed within headpiece 106, one or more microphones disposed within sound processor 104, one or more beam-forming microphones, and/or any other suitable microphone as may serve a particular implementation.

Sound processor 104 (i.e., one or more components included within sound processor 104) may be configured to direct cochlear implant 108 to generate and apply electrical stimulation (also referred to herein as "stimulation current") representative of one or more audio signals (e.g., one or more audio signals detected by microphone 102, input by way of an auxiliary audio input port, etc.) to one or more stimulation sites associated with an auditory pathway (e.g., the auditory nerve) of the patient. Exemplary stimulation sites include, but are not limited to, one or more locations within the cochlea, the cochlear nucleus, the inferior colliculus, and/or any other nuclei in the auditory pathway. To this end, sound processor 104 may process the one or more audio signals in accordance with a selected sound processing strategy or program to generate appropriate stimulation parameters for controlling cochlear implant 108. Sound processor 104 may include or be implemented by a behind-the-ear ("BET") unit, a body worn device, and/or any other sound processing unit as may serve a particular implementation. For example, sound processor 104 may be implemented by an electro-acoustic stimulation ("EAS") sound processor included in an EAS system configured to provide electrical and acoustic stimulation to a patient.

Headpiece 106 may be communicatively coupled to sound processor 104 and may include various components configured to facilitate selective wireless coupling of sound processor 104 to cochlear implant 108. To this end, headpiece 106 may be configured to be affixed to the recipient's head so as to transmit commands (e.g., stimulation parameters) and/or RF power wirelessly between sound processor 104 and cochlear implant 108 via a wireless communication link 114 (which may include a bi-directional communication link and/or one or more dedicated uni-directional communication links as may serve a particular implementation). Exemplary components that may be included in Headpiece 106 to facilitate wireless communication link 114 are described herein.

In some examples, sound processor 104 may wirelessly transmit stimulation parameters (e.g., in the form of data words included in a forward telemetry sequence) and/or RF power to cochlear implant 108 by way of wireless communication link 114 between headpiece 106 and cochlear implant 108.

Cochlear implant 108 may include any type of implantable stimulator that may be used in association with the systems and methods described herein. For example, cochlear implant 108 may be implemented by an implantable stimulator. In some alternative implementations, cochlear implant 108 may include a brainstem implant and/or any other type of active implant or auditory prosthesis that may be implanted within a recipient and configured to apply stimulation to one or more stimulation sites located along an auditory pathway of a recipient.

In some examples, cochlear implant 108 may be configured to generate electrical stimulation representative of an audio signal processed by sound processor 104 (e.g., an audio signal detected by microphone 102) in accordance with one or more stimulation parameters transmitted thereto by sound processor 104. Cochlear implant 108 may be further configured to apply the electrical stimulation to one or more stimulation sites within the recipient via one or more electrodes 112 disposed along lead 110 (e.g., by way of one or more stimulation channels formed by electrodes 112). In some examples, cochlear implant 108 may include a plurality of independent current sources each associated with a channel defined by one or more of electrodes 112. In this manner, different stimulation current levels may be applied to multiple stimulation sites simultaneously (also referred to as "concurrently") or sequentially by way of multiple electrodes 112.

Figure 2:
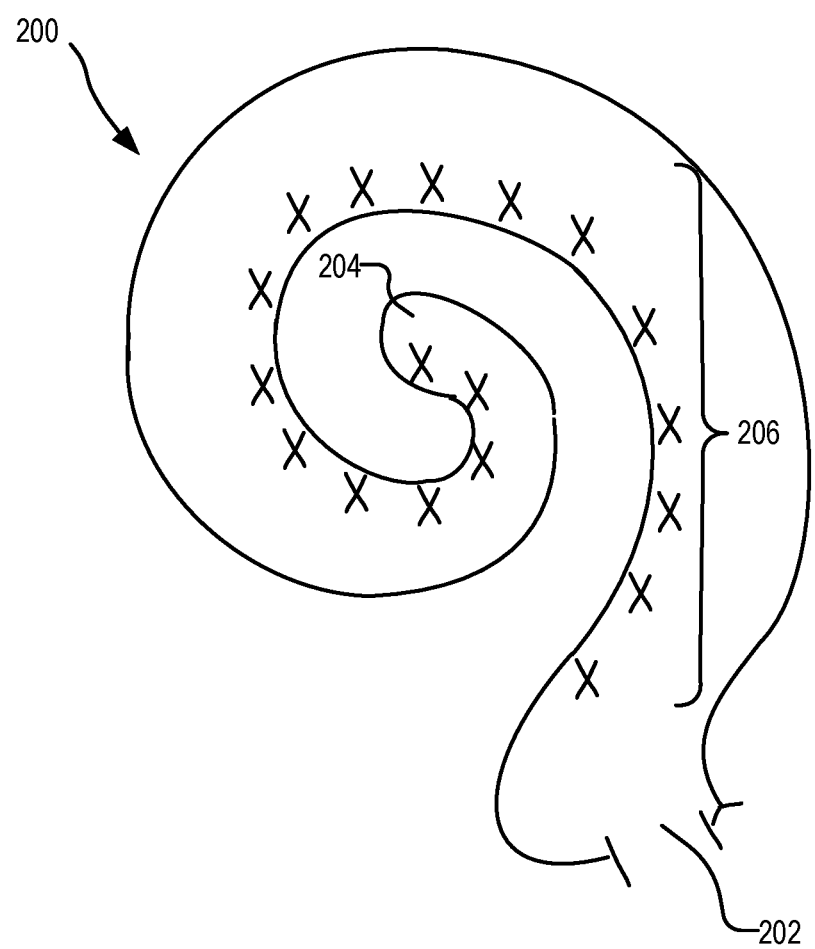
FIG. 2 illustrates a schematic structure of the human cochlea.

FIG. 2 illustrates a schematic structure of the human cochlea 200 into which lead 110 may be inserted. As shown in FIG. 2, the cochlea 200 is in the shape of a spiral beginning at a base 202 and ending at an apex 204. Within the cochlea 200 resides auditory nerve tissue 206, which is denoted by Xs in FIG. 2. The auditory nerve tissue 206 is organized within the cochlea 200 in a tonotopic manner. Relatively low frequencies are encoded at or near the apex 204 of the cochlea 200 (referred to as an "apical region") while relatively high frequencies are encoded at or near the base 202 (referred to as a "basal region"). Hence, each location along the length of the cochlea 200 corresponds to a different perceived frequency. Cochlear implant system 100 may therefore be configured to apply electrical stimulation to different locations within the cochlea 200 (e.g., different locations along the auditory nerve tissue 206) to provide a sensation of hearing.

Figure 3:
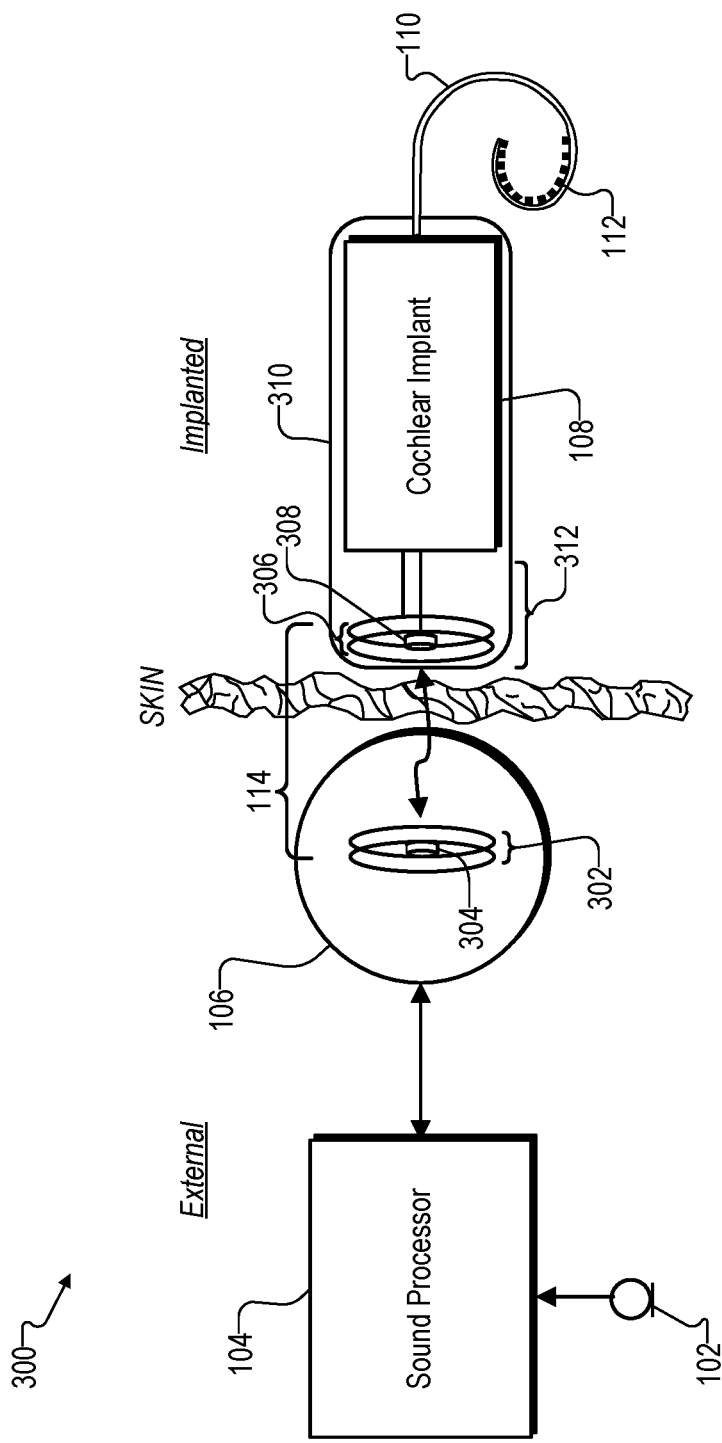
FIG. 3 illustrates an exemplary configuration of the cochlear implant system shown in FIG. 1 according to principles described herein.

FIG. 3 shows an exemplary configuration 300 of cochlear implant system 100 in which a headpiece antenna 302 and a headpiece magnet 304 are included as components within headpiece 106. FIG. 3 also shows a cochlear implant antenna 306 and a cochlear implant magnet 308 that are implanted within the recipient. As shown in FIG. 3, headpiece antenna 302 is provided external to the recipient and communicatively couples with cochlear implant antenna 306, which is communicatively coupled to cochlear implant 108. Headpiece antenna 302 is configured to transcutaneously transmit RF power and/or commands to cochlear implant 108 by way of wireless communication link 114 and cochlear implant antenna 306. Headpiece magnet 304 is configured to interact with cochlear implant magnet 308 so as to maintain headpiece 106 at a predefined position with respect to cochlear implant 108 while headpiece 106 is worn on the head of the recipient.

In the example shown in FIG. 3, cochlear implant antenna 306 is shown as having two coils that are coiled in an oval shape. However, it is understood that a single wire that has multiple turns may be provided in certain examples. In addition, the coils or multiple turns of a coil of a cochlear implant antenna may have any suitable shape, size, and/or number of coils/turns as may serve a particular implementation. For example, the coils included in cochlear implant antenna 306 may be coiled in a square shape, a rectangular shape, a triangular shape, a circular shape or any other suitable shape in certain implementations.

As shown in FIG. 3, cochlear implant 108 and cochlear implant antenna 306 are covered by an encapsulant 310, which is provided to protect certain components of a cochlear implant system while such components are implanted within a recipient. The combination of cochlear implant 108, antenna 306, and encapsulant 310 may be generally referred to as a cochlear implant assembly. Cochlear implant assemblies such as those described herein may include additional components in other implementations. As such, encapsulant 310 may also encapsulate other implantable components of a cochlear implant system (e.g., cochlear implant system 100) in other implementations.

Encapsulant 310 may be formed of any suitable biocompatible insulative material. For example, encapsulant 310 may be formed of medical grade silicone, polyurethane, a thermoplastic elastomer, and/or any other suitable material.

Encapsulant 310 may be formed in any suitable manner as may serve a particular implementation. In certain examples, encapsulant 310 may be overmolded around certain implantable components (e.g., cochlear implant 108, electrode lead 110, cochlear implant antenna 306, cochlear implant magnet 308, etc.) included in cochlear implant system 100. Alternatively, encapsulant 310 may be formed through casting, spraying, dipping, or any other suitable manufacturing method.

In some cochlear implants, an encapsulant that covers a cochlear implant antenna includes a guard wire configured to confine an electric field associated with the cochlear implant antenna. However, as mentioned above, such guard wires are difficult to manufacture and may be easily damaged (e.g., due to an impact to the head of the recipient). Hence, as shown in FIG. 3, encapsulant 310 does not include a guard wire wrapped spirally around the coils of cochlear implant antenna 306. Instead, encapsulant 310 is impregnated with a dielectric material that is configured to reduce fringing of the electric field associated with cochlear implant antenna 306 into the surrounding tissue and confine the electric field.

The dielectric material may include any suitable high permittivity, low loss dielectric material that may be provided around the coils of cochlear implant antenna 306. The dielectric material may have a high relative permittivity (e.g., around or above 50) and a low dissipation factor (e.g., approximately 0.0001). In certain examples, the dielectric material impregnated in encapsulant 310 may include one or more of titanium dioxide, calcium titanate, titanium silicon oxide, and any other suitable dielectric material. The dielectric material may be formed of a single material (e.g., only titanium dioxide) or any suitable combination of different dielectric materials that may be impregnated within encapsulant 310.

In certain examples, the dielectric material may be impregnated within a material of encapsulant 310 that already has a relatively high dielectric strength. For example, as noted above, in certain examples, encapsulant 310 may be formed of silicone, which has a high dielectric strength as compared to other polymers. In such examples, the dielectric material may be impregnated in encapsulant 310 to give at least a portion of the silicone forming encapsulant 310 a higher relative permittivity (i.e., a higher dielectric constant) than the silicone would otherwise have without the dielectric material impregnated therein.

The dielectric material may be impregnated within encapsulant 310 in any suitable form. For example, the dielectric material may be provided as a dielectric powder that is mixed into the material used to form encapsulant 310 prior to or during manufacture of the cochlear implant assembly.

Any suitable amount of dielectric material may be impregnated within encapsulant 310 as may serve a particular implementation. In certain examples, encapsulant 310 may include a predetermined percentage by weight of dielectric material. For example, encapsulant 310 may include approximately 50% by weight of the dielectric material in certain implementations.

The dielectric material may be provided in any suitable portion or region of encapsulant 310 as may serve a particular implementation. In certain examples, the dielectric material may be evenly distributed throughout all of encapsulant 310. In such examples, the dielectric material would be exposed to an external surface of the cochlear implant assembly and, as a result, would be in contact with the surrounding tissue when the cochlear implant assembly is implanted within the recipient. In such examples, dielectric materials that suppress biofilm formation (e.g., titanium dioxide) may be impregnated within encapsulant 310 for the added benefit of preventing or mitigating biofilm formation on a surface of the cochlear implant assembly.

In certain alternative examples, the dielectric material may only be provided in a certain region of encapsulant 310. To illustrate, in the example shown in FIG. 3, the dielectric material may only be provided in a region 312 of encapsulant 310 that includes cochlear implant antenna 306.

In certain examples, encapsulant 310 may be opaque or transparent depending on the particular dielectric material impregnated therein. For example, if a dielectric material such as titanium dioxide, which has a white pigment, is evenly distributed within encapsulant 310, all of encapsulant 310 may be opaque. In certain other examples, only a region of encapsulant 310 that includes the dielectric material may be opaque. For example, region 312 shown in FIG. 3 may be opaque while a remainder of encapsulant 310 that does not include the dielectric material may be transparent. In certain alternative examples, region 312 may be impregnated with a dielectric material that does not cause encapsulant 310 to be opaque. Accordingly, in certain examples, encapsulant 310 may be transparent in a region (e.g., region 312) that covers cochlear implant antenna 306 such that cochlear implant antenna 306 is visible through encapsulant 310 and the dielectric material.

In certain examples, encapsulant 310 and the dielectric material impregnated therein may be in direct contact with a wire that forms cochlear implant antenna 306. Alternatively, the wire that forms cochlear implant antenna 306 may include an insulative coating that is provided between the wire and encapsulant 310. Exemplary implementations in which a cochlear implant antenna includes a wire with an insulating coating will now be described with reference to FIGS. 4-7.

Figure 4:
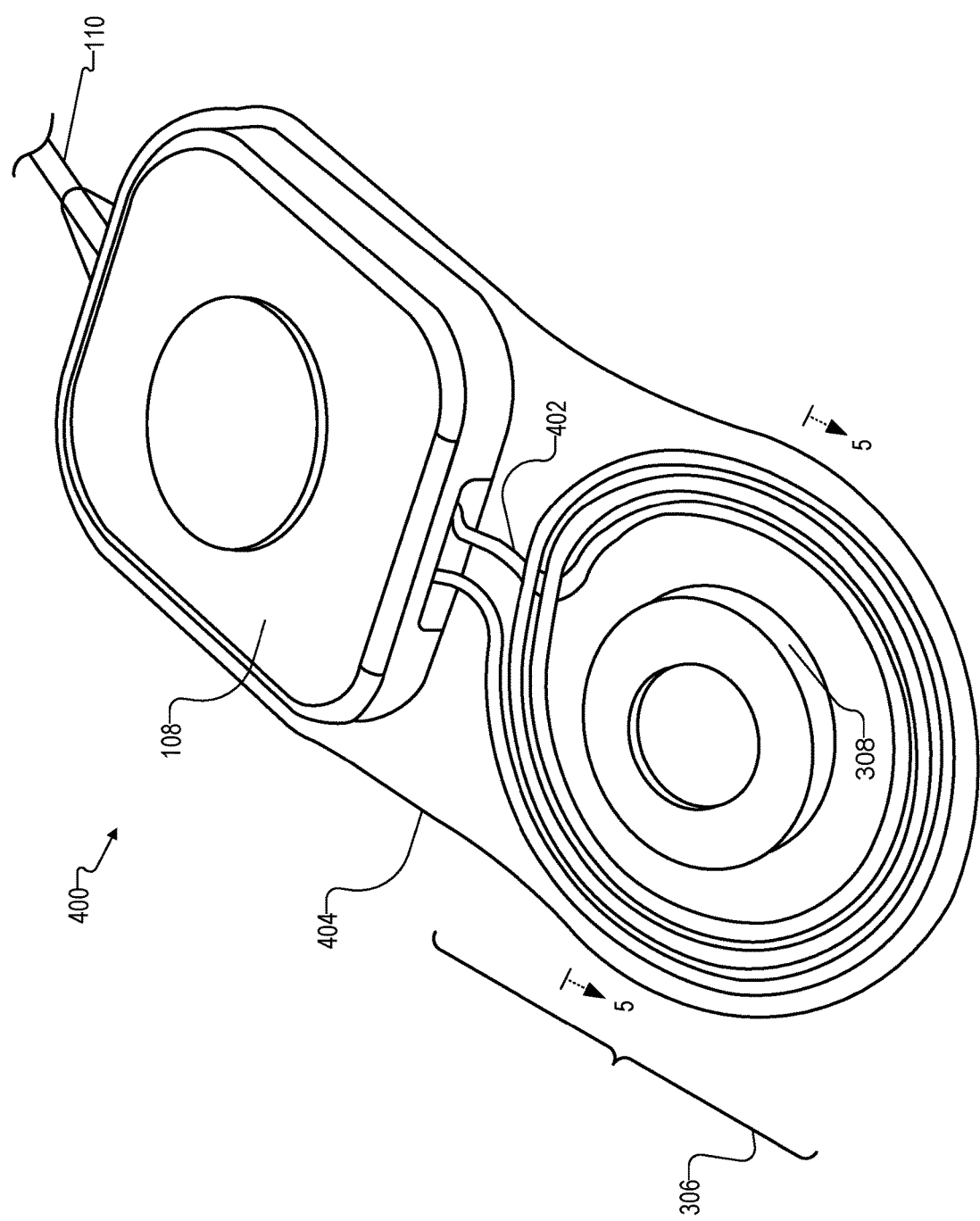
FIG. 4 illustrates an exemplary cochlear implant assembly according to principles described herein.

FIG. 4 illustrates an exemplary cochlear implant assembly 400 that may be provided in certain examples. As shown in FIG. 4, cochlear implant assembly 400 includes cochlear implant 108, cochlear implant antenna 306 that comprises a wire 402 that is communicatively connected to cochlear implant 108, and an encapsulant 404. In the example shown in FIG. 4, wire 402 of cochlear implant antenna 306 is in a coiled configuration that has a circular shape. As shown in FIG. 4, cochlear implant magnet 308 is provided at a center of the circular shape of coiled wire 402 to facilitate positioning headpiece antenna 302 with respect to cochlear implant antenna 306.

Although FIG. 4 shows wire 402 of cochlear implant antenna 306 as having three turns that form a coil, it is understood that a coil of a cochlear implant antenna may have any suitable number of turns as may serve a particular implementation.

FIG. 4 shows encapsulant 404 as being transparent such that cochlear implant antenna 306 is visible through encapsulant 404. However, as mentioned herein, in certain examples, encapsulant 404 may be opaque such that cochlear implant antenna 306 is not visible in a region of encapsulant 404 that includes the dielectric material.

Figure 5:
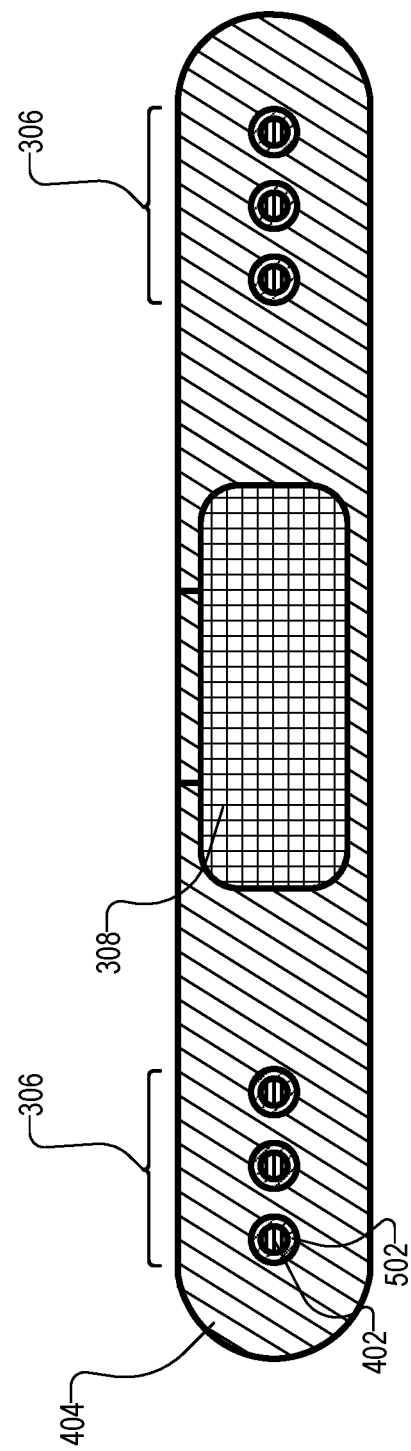
FIG. 5 is an exemplary cross section of the cochlear implant assembly shown in FIG. 4 that is taken along lines 5-5 in FIG. 4 according to principles described herein.

FIG. 5 depicts a cross-sectional view of cochlear implant assembly 400 taken along lines 5-5 in FIG. 4. As shown in FIG. 5, cochlear implant antenna 306 is formed of wire 402 and an insulative coating 502. Any suitable type of wire may be used for cochlear implant antenna 306 as may serve a particular implementation. For example, the wire may be formed of any suitable metal usable to inductively receive RF power and/or commands from a sound processor.

Insulative coating 502 has a relatively low dielectric constant (e.g., as compared to the dielectric material) and is provided to facilitate spacing of the turns of the coil of cochlear implant antenna 306 uniformly with respect to each other, reducing interwinding capacitance, and preserving a proper self-resonant frequency for cochlear implant antenna 306. Insulative coating 502 may be formed of any suitable material as may serve a particular implementation. For example, insulative coating 502 may be formed of a low dielectric silicone elastomer. It is understood that insulative coating 502 is not impregnated with the dielectric material.

As shown in FIG. 5, encapsulant 404 and the dielectric material impregnated therein are in direct contact with insulative coating 502 of cochlear implant antenna 306.

Although FIG. 5 shows adjacent windings of wire 402 as being separated from each other by portions encapsulant 402, it is understood that in certain examples coatings 502 of adjacent windings of wire 402 may be in direct contact with each other. For example, coating 502 of the leftmost winding shown in FIG. 5 may be in direct contact in a horizontal direction with coating 502 of the winding that is second from the left. Similarly, coating 502 of the winding that is second from the left may be in direct contact in the horizontal direction with coating 502 of the winding that is third from the left in FIG. 5.

In the example shown in FIG. 5, a dielectric material may be distributed throughout encapsulant 404 such that wire 402 and insulative coating 502 are either completely or at least partially surrounded by the dielectric material. In so doing, it is possible to confine an electric field associated with cochlear implant antenna 306 without having to wrap a guard wire around the turns of the coil of cochlear implant antenna 306.

Figure 6:
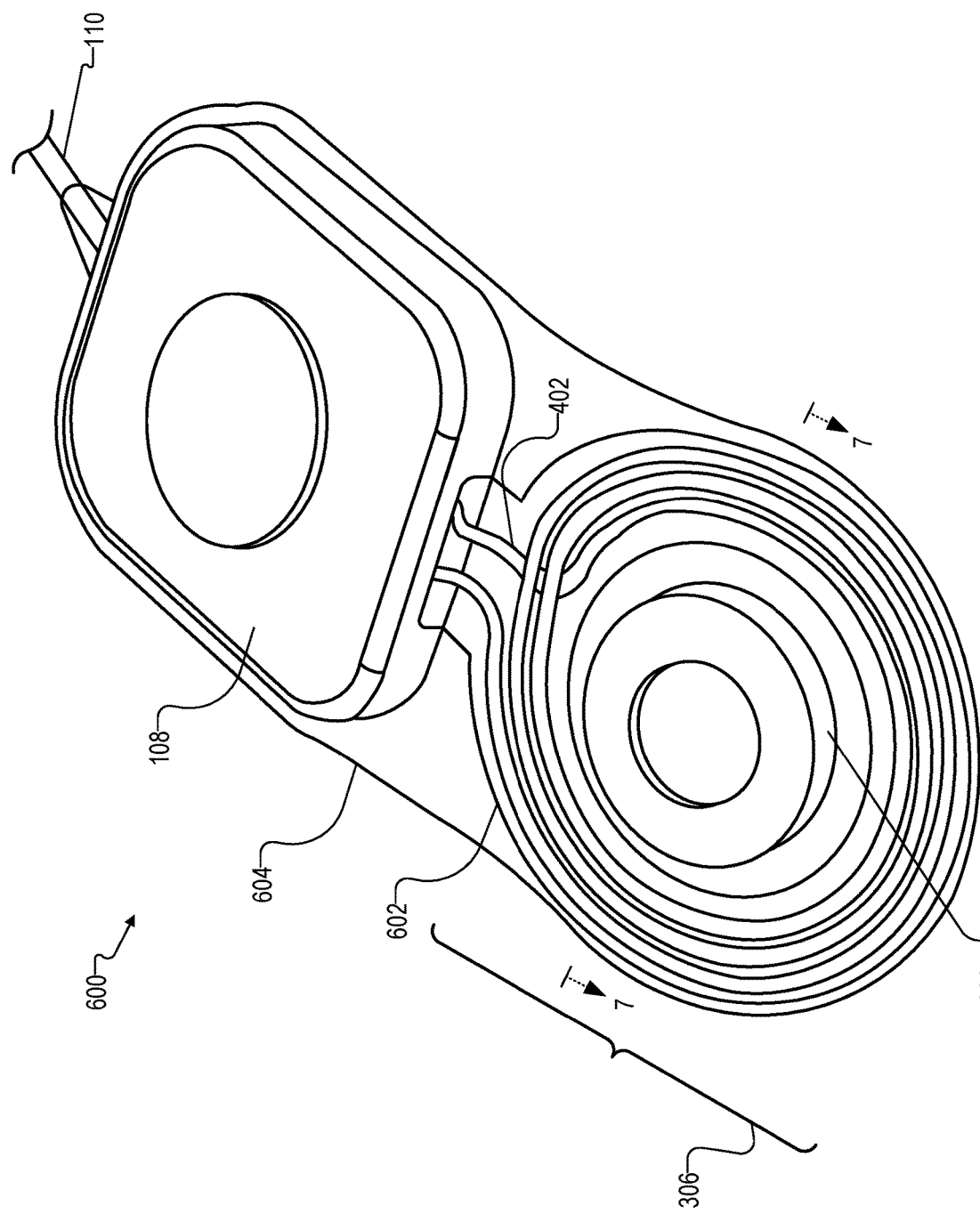
FIG. 6 illustrates another exemplary cochlear implant assembly according to principles described herein.

FIG. 6 shows another exemplary cochlear implant assembly 600 that may be provided in certain examples. As shown in FIG. 6, cochlear implant antenna 306 is covered by a first encapsulant 602 that is impregnated with a dielectric material that is configured to confine an electric field around cochlear implant antenna 306. A second encapsulant 604 covers cochlear implant 108 and cochlear implant antenna 306 that is covered by first encapsulant 602. As shown in FIG. 6, first encapsulant 602 does not include a guard wire coiled around an outer surface of first encapsulant 602.

Although FIG. 6 shows wire 402 of cochlear implant antenna 306 as having three turns that form a coil, it is understood that a coil of a cochlear implant antenna may have any suitable number of turns as may serve a particular implementation.

FIG. 6 shows first encapsulant 602 and second encapsulant 604 as being transparent such that cochlear implant antenna 306 is visible through first encapsulant 602 and second encapsulant 604. However, as mentioned herein, in certain examples, first encapsulant 602 may be opaque and second encapsulant 604 may be transparent. For example, first encapsulant 602 may be impregnated with titanium dioxide, which may cause first encapsulant 602 to have a white pigment. Second encapsulant 604 on the other hand may be formed, for example, of medical grade silicone, which may be transparent. Alternatively, both first encapsulant 602 and second encapsulant 604 may be opaque in certain examples (e.g., both first encapsulant 602 and second encapsulant 604 may be impregnated with a dielectric material such as titanium dioxide).

Figure 7:
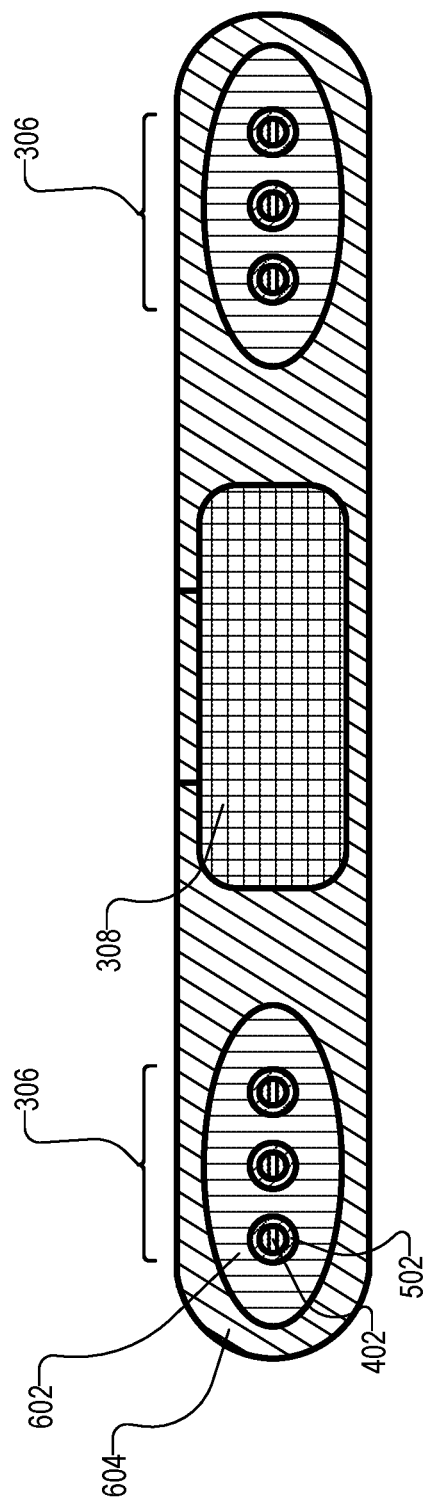
FIG. 7 is an exemplary cross section of the cochlear implant assembly shown in FIG. 6 that is taken along lines 7-7 in FIG. 6 according to principles described herein.

FIG. 7 depicts a cross-sectional view of cochlear implant assembly 600 taken along line 7-7 in FIG. 6. As shown in FIG. 7, cochlear implant antenna 306 is provided within first encapsulant 602 such that wire 402 and insulative coating 502 are completely surrounded by first encapsulant 602 and the dielectric material impregnated therein.

Wire 402 and insulative coating 502 shown in FIG. 7 may be configured in a manner similar to that described above with respect to FIG. 5.

In the example shown in FIG. 7, first encapsulant 602 is illustrated as having an oval cross-sectional shape. However, first encapsulant 602 may have any other suitable cross-sectional shape (e.g., square, circular, rectangular, etc.) as may serve a particular implementation.

In certain alternative implementations, the dielectric material may be provided in second encapsulant 604 instead of first encapsulant 602. In such examples, first encapsulant 602 and insulative coating 502 may each be formed of a material having a relatively low permittivity as compared to second encapsulant 604 with the dielectric material impregnated therein.

Figure 8:
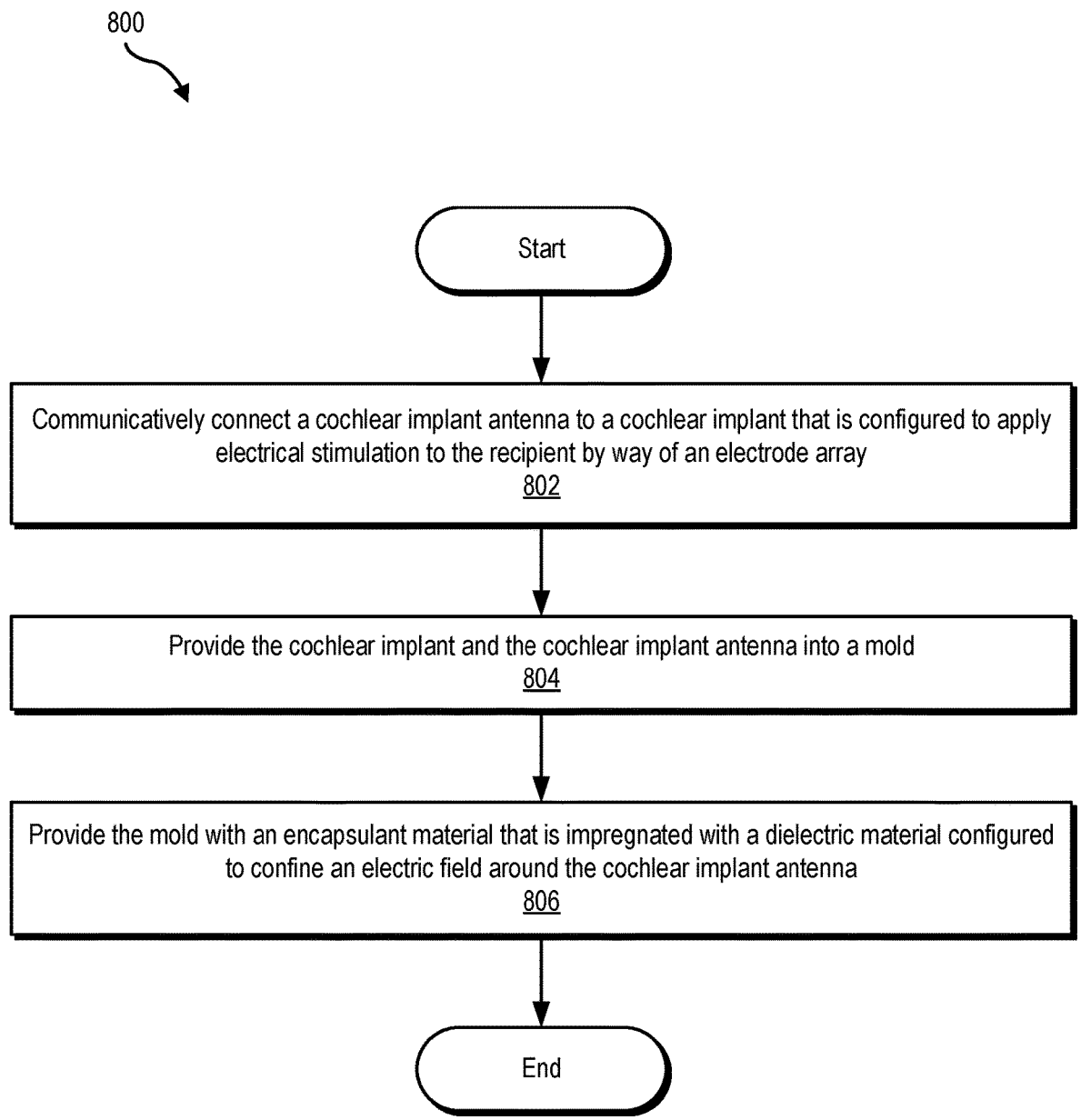
FIG. 8 illustrates an exemplary method for manufacturing a cochlear implant assembly according to principles described herein.

FIG. 8 illustrates an exemplary method 800 for manufacturing a cochlear implant assembly (e.g., cochlear implant assembly 400). While FIG. 8 illustrates exemplary steps according to one embodiment, other embodiments may omit, add to, reorder, and/or modify any of the steps shown in FIG. 8.

In operation 802, a cochlear implant antenna is communicatively connected to a cochlear implant. As described herein, the cochlear implant is configured to apply electrical stimulation to a recipient by way of an electrode array. The cochlear implant antenna may comprise a wire that is covered in an insulative coating. Operation 802 may be performed in any of the ways described herein.

In operation 804, the cochlear implant and the cochlear implant antenna are provided into a mold. Operation 804 may be performed in any of the ways described herein.

In operation 806, the mold is provided with an encapsulant material that is impregnated with a dielectric material configured to confine an electric field around the cochlear implant antenna. The encapsulant material may be provided into the mold in such a manner that the encapsulant material forms an encapsulant that covers the cochlear implant and the cochlear implant antenna. In certain examples, the encapsulant may completely cover the cochlear implant and the cochlear implant antenna. Operation 806 may be performed in any of the ways described herein.

With the operations included in method 800 is it possible to reduce the number of operations used to manufacture cochlear implant assemblies such as those described herein as compared to methods for manufacturing conventional cochlear implant assemblies. For example, in certain examples, it is possible to eliminate an operation where, for example, an intermediate overmold is provided over a cochlear implant antenna to facilitate winding a guard wire. That is, in certain examples, only one encapsulation operation (e.g., overmold operation) may be performed. Further, it is possible to eliminate a manually intensive operation of winding a guard wire around the intermediate overmold and a connecting operation in which the guard wire is, for example, welded to a cochlear implant.

In certain alternative examples, operation 806 may include forming a first encapsulant by encapsulating the cochlear implant antenna with a first portion of the encapsulant material that includes the dielectric material. After forming the first encapsulant, operation 806 may further include forming a second encapsulant by covering the cochlear implant and the first encapsulant with a second portion of the encapsulant material. In such examples, the first encapsulant and the second encapsulant together form the encapsulant that covers the cochlear implant antenna and the cochlear implant.

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:

1. A cochlear implant assembly adapted for insertion into a recipient, comprising:
    a cochlear implant configured to apply electrical stimulation to the recipient by way of an electrode array;
    a cochlear implant antenna communicatively coupled to the cochlear implant;
    a first encapsulant that covers the cochlear implant and the cochlear implant antenna, the first encapsulant impregnated with a dielectric material that is configured to confine an electric field around the cochlear implant antenna; and
    a second encapsulant that is covered by the first encapsulant and that covers the cochlear implant antenna, the second encapsulant not impregnated with the dielectric material,
    wherein:
        the first encapsulant impregnated with the dielectric material completely surrounds the cochlear implant antenna; and
        the dielectric material is evenly distributed throughout the first encapsulant.

2. The cochlear implant assembly of claim 1, wherein the first encapsulant is opaque in a region that covers the cochlear implant antenna.

3. The cochlear implant assembly of claim 1, wherein the first encapsulant is transparent in a region that covers the cochlear implant antenna such that the cochlear implant antenna is visible through the first encapsulant.

4. The cochlear implant assembly of claim 1, wherein the cochlear implant antenna includes a wire that is covered in an insulative coating.

5. The cochlear implant assembly of claim 1, wherein the dielectric material is configured to suppress biofilm formation on a surface of the cochlear implant assembly.

6. The cochlear implant assembly of claim 1, wherein:
    the first encapsulant is formed of silicone; and
    the dielectric material impregnated in the silicone is one or more of titanium dioxide, calcium titanate, and titanium silicon oxide.

7. A cochlear implant assembly adapted for insertion into a recipient, comprising:
    a cochlear implant configured to apply electrical stimulation to the recipient by way of an electrode array;
    a cochlear implant antenna communicatively coupled to the cochlear implant;
    a first encapsulant that covers the cochlear implant antenna, the first encapsulant impregnated with a dielectric material that is configured to confine an electric field around the cochlear implant antenna; and
    a second encapsulant that covers the cochlear implant and the cochlear implant antenna that is covered with the first encapsulant, the second encapsulant not impregnated with the dielectric material,
    wherein:
        the first encapsulant does not include a guard wire coiled around an outer surface of the first encapsulant;
        the first encapsulant impregnated with the dielectric material completely surrounds the cochlear implant antenna; and
        the dielectric material is evenly distributed throughout the first encapsulant.

8. The cochlear implant assembly of claim 7, wherein:
    the first encapsulant is opaque; and
    the second encapsulant is transparent.

9. The cochlear implant assembly of claim 7, wherein both the first encapsulant and the second encapsulant are transparent.

10. The cochlear implant assembly of claim 7, wherein the cochlear implant antenna includes a wire that is covered in an insulative coating.

11. The cochlear implant assembly of claim 7, wherein the dielectric material is configured to suppress biofilm formation on a surface of the cochlear implant assembly.

12. The cochlear implant assembly of claim 7, wherein:
    the first encapsulant is formed of silicone; and
    the dielectric material impregnated in the silicone is one or more of titanium dioxide, calcium titanate, and titanium silicon oxide.

13. A method of manufacturing a cochlear implant assembly adapted for insertion into a recipient, the method comprising:
    communicatively connecting a cochlear implant antenna to a cochlear implant that is configured to apply electrical stimulation to the recipient by way of an electrode array, the cochlear implant antenna comprising a wire that is covered in an insulative coating;
    providing a cochlear implant and the cochlear implant antenna into a mold; and
    providing the mold with an encapsulant material that is impregnated with a dielectric material configured to confine an electric field around the cochlear implant antenna, the providing of the mold with the encapsulant material comprising:
        forming a first encapsulant by encapsulating the cochlear implant antenna with a first portion of the encapsulant material that includes the dielectric material; and
        forming a second encapsulant by covering the cochlear implant and the first encapsulant with a second portion of the encapsulant material that does not include the dielectric material,
    wherein:
        the first encapsulant and the second encapsulant cover the cochlear implant and the cochlear implant antenna;
        the first encapsulant impregnated with the dielectric material completely surrounds the cochlear implant antenna; and
        the dielectric material is evenly distributed throughout the first encapsulant.

14. The method of claim 13, wherein the first portion of the encapsulant material is opaque.

15. The method of claim 13, wherein the first portion of the encapsulant material is transparent.

16. The method of claim 13, wherein:
the encapsulant material is silicone; and
the dielectric material impregnated in the silicone is one or more of titanium dioxide, calcium titanate, and titanium silicon oxide.

17. The method of claim 13, wherein the cochlear implant antenna is provided in a coiled configuration.

18. The method of claim 13, wherein the first encapsulant that is impregnated with the dielectric material is in direct contact with the insulative coating of the cochlear implant antenna.

* * * * *